US00PP34530P2

(12) United States Plant Patent
Ammerlaan

(10) Patent No.: US PP34,530 P2
(45) Date of Patent: Aug. 30, 2022

(54) ***ECHEVERIA* PLANT NAME 'OVPEARLS14'**

(50) Latin Name: ***Echeveria pulidonis* x *gibbiflora***
Varietal Denomination: OVPEARLS14

(71) Applicant: Ovata B.V., Bleiswijk (NL)

(72) Inventor: Johannes Hendrikus Adrianus Ammerlaan, Bleiswijk (NL)

(73) Assignee: Ovata B.V., Bleiswijk (NL)

( * ) Notice: Subject to any disclaimer, the term of this patent is extended or adjusted under 35 U.S.C. 154(b) by 0 days.

(21) Appl. No.: 17/803,289

(22) Filed: Apr. 21, 2022

(51) Int. Cl.
*A01H 5/12* (2018.01)
*A01H 6/32* (2018.01)

(52) U.S. Cl.
USPC ..... Plt./373

(58) Field of Classification Search
USPC ..... Plt./373
See application file for complete search history.

*Primary Examiner* — Karen M Redden
(74) *Attorney, Agent, or Firm* — Samuel R. McCoy, Jr.

(57) ABSTRACT

A new and distinct variety of *Echeveria* plant named 'OVPEARLS14' which is characterized by a globular profile with foliage that is tightly held in a basal rosette, relatively long and concave oblanceolate foliage, foliar margins that are occasionally very lightly crenulate to denticulate along one side of the lamina, at and near the apex, glaucous foliage that is covered with a layer of greyed-green epicuticular wax which gives the foliage a dark blue-grey appearance, juvenile foliage that is lightly suffused with greyed-purple along the distal portion of the margins and laminar tips, and mature foliage with dark greyed-orange foliar margins and a greyed-purple laminar tip. The new variety has shown to be uniform and stable in the resulting generations from asexual propagation.

4 Drawing Sheets

Latin name of the genus and species: The Latin name of the genus and species of the novel variety disclosed herein is *Echeveria pulidonis* x *gibbiflora*.

Variety denomination: The inventive variety of *Echeveria* disclosed herein has been given the variety denomination 'OVPEARLS14'.

BACKGROUND OF THE INVENTION

Parentage: 'OVPEARLS14' is a seedling selection, presumed to be the result of the open pollination of an unnamed *Echeveria pulidonis* plant (unpatented), the seed parent, and a plurality of unnamed *Echeveria gibbiflora* plants (not patented), the presumed pollen parent. The exact pollen parent is unknown. The crossing is believed to have occurred in the summer of 2016 at a commercial greenhouse in Bleiswijk, the Netherlands. In early 2017, one seedling from said cross was observed to exhibit unique foliage and growth characteristics when compared to the parent plants and all other progeny. After confirming the stability of the unique characteristics first observed, the new plant was selected for commercialization and given the name, 'OVROCKS09'.

Asexual Reproduction: Asexual reproduction of the new cultivar 'OVPEARLS14', by way of rooting leaf cuttings, was first initiated in the autumn of 2017 at the inventor's commercial greenhouse in Bleiswijk, the Netherlands. Through eleven subsequent generations, the unique features of this cultivar have proven to be stable and true to type.

SUMMARY OF THE INVENTION

The cultivar 'OVPEARLS14' has not been observed under all possible environmental conditions. The phenotype may vary somewhat with variations in environment such as temperature, day length, and light intensity, without, however, any variance in genotype. The following traits have been repeatedly observed and are determined to be the unique characteristics of 'OVPEARLS14'. These characteristics in combination distinguish 'OVPEARLS14' as a new and distinct *Echeveria* cultivar:

1. 'OVPEARLS14' exhibits a large amount of succulent foliage that is tightly held in a compact basal rosette with a globular profile; and
2. 'OVPEARLS14' exhibits relatively long, concave, oblanceolate foliage with an upright attitude; and
3. 'OVPEARLS14' and foliar margins that are occasionally very lightly crenulate to denticulate along one side of the lamina, at and near the apex; and
4. 'OVPEARLS14' exhibits glaucous foliage that is covered with a layer of greyed-green epicuticular wax which gives the foliage a dark blue-grey appearance; and
5. 'OVPEARLS14' exhibits juvenile foliar margins that are lightly suffused with greyed-purple along the distal margins and laminar tip; and
6. 'OVPEARLS14' exhibits mature foliage with dark greyed-orange foliar margins and a greyed-purple laminar tip.

BOTANICAL DESCRIPTION OF THE PLANT

Figure 1:
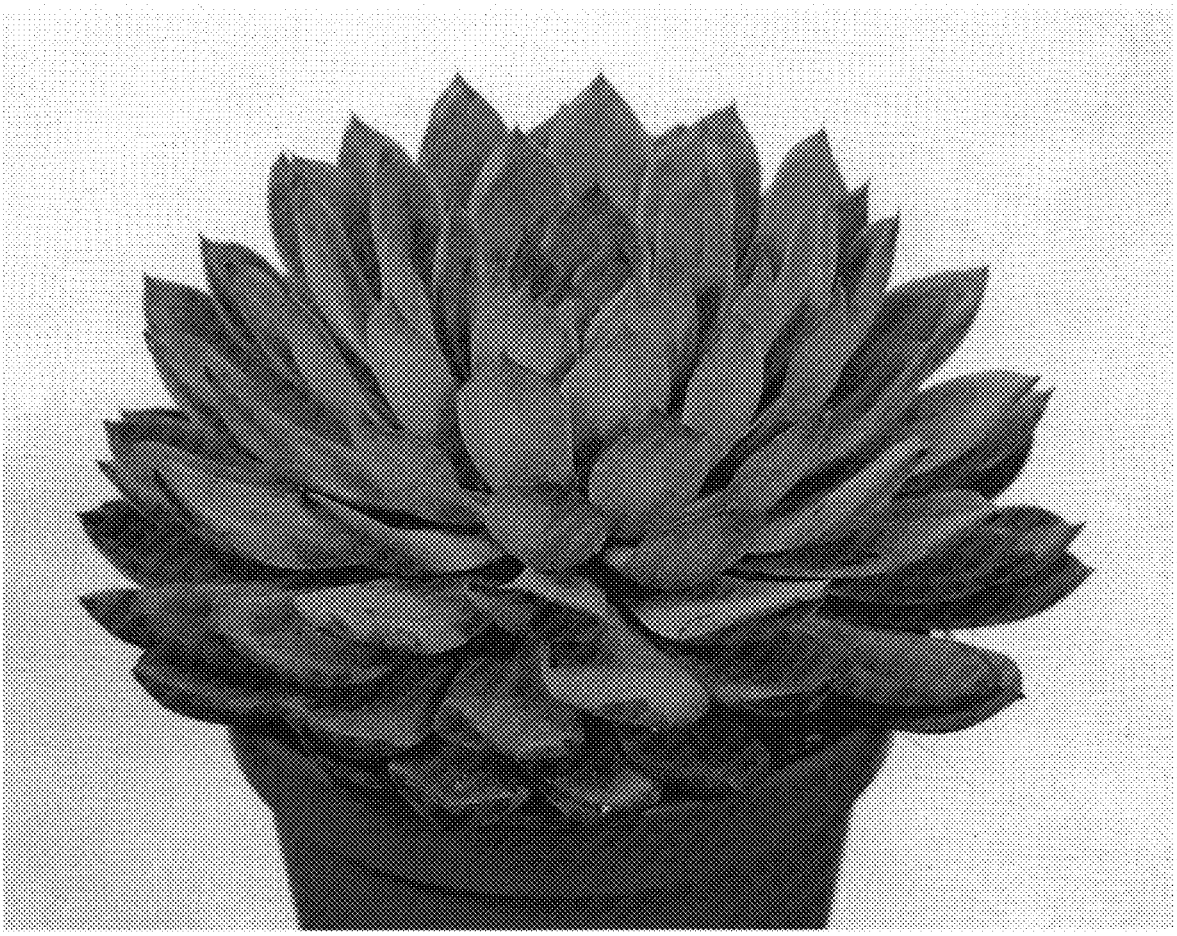
FIG. 1 illustrates, as nearly true as it is reasonably possible to make the same in color photographs of this type, an exemplary plant of 'OVPEARLS14' grown in a commercial greenhouse in Bleiswijk, the Netherlands. This plant is approximately 1.5-year-old, shown planted in a 15 cm container.
Figure 2:
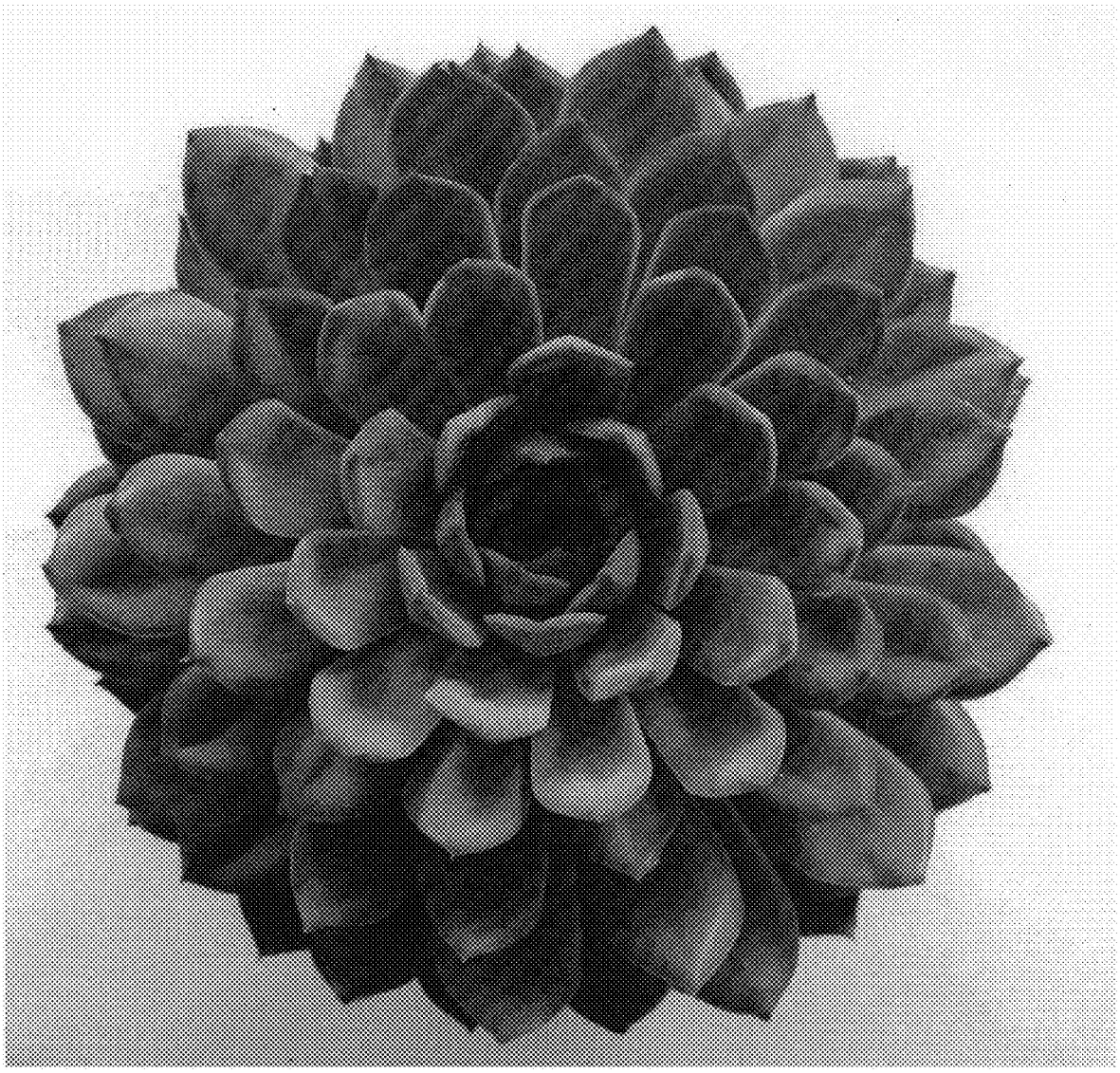
FIG. 2 illustrates, as nearly true as it is reasonably possible to make the same in color photographs of this type, the typical foliage arrangement of 'OVPEARLS14'.
Figure 3:
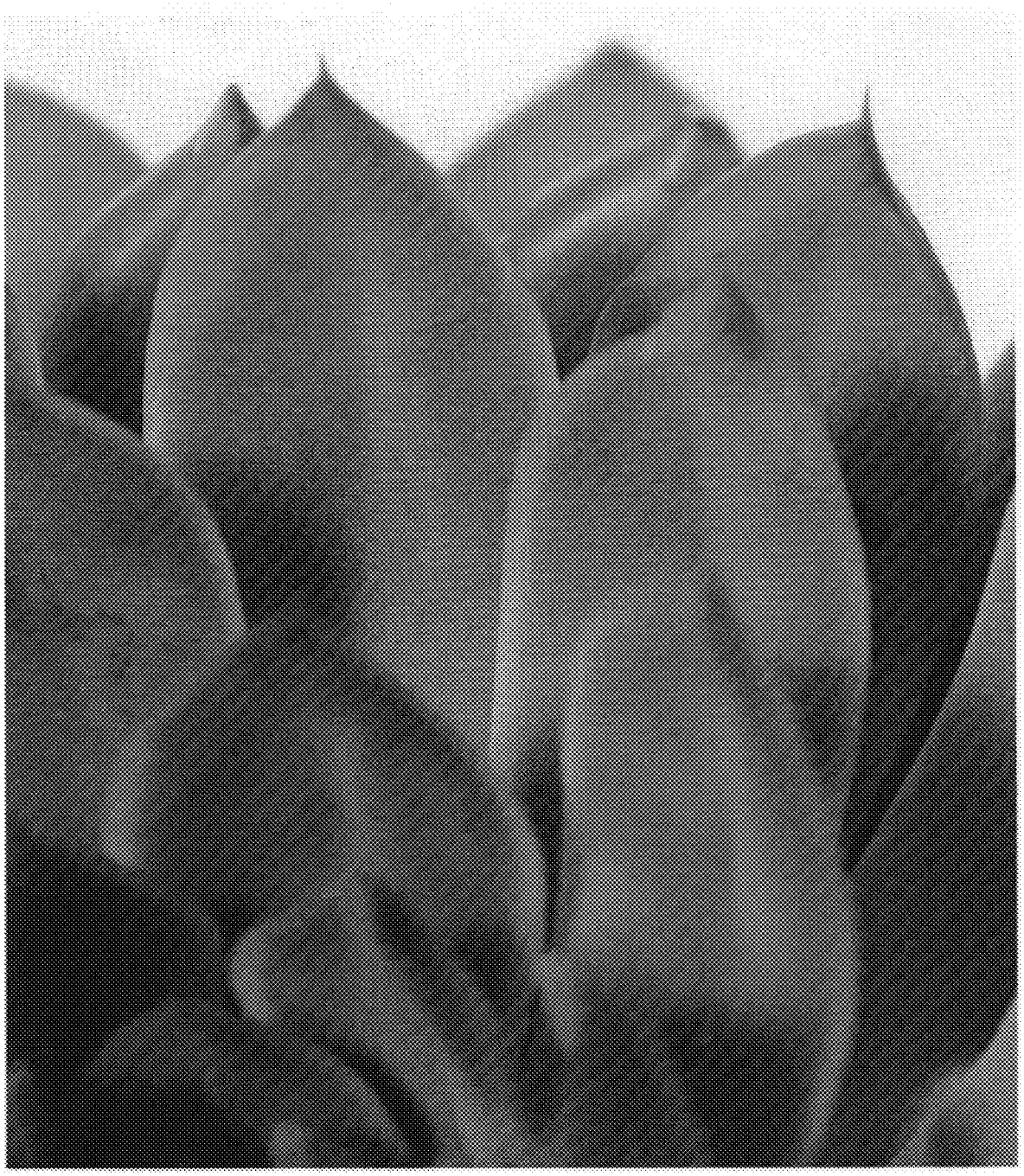
FIG. 3 illustrates, as nearly true as it is reasonably possible to make the same in color photographs of this type, the adaxial surface of the mature foliage 'OVPEARLS14'.
Figure 4:
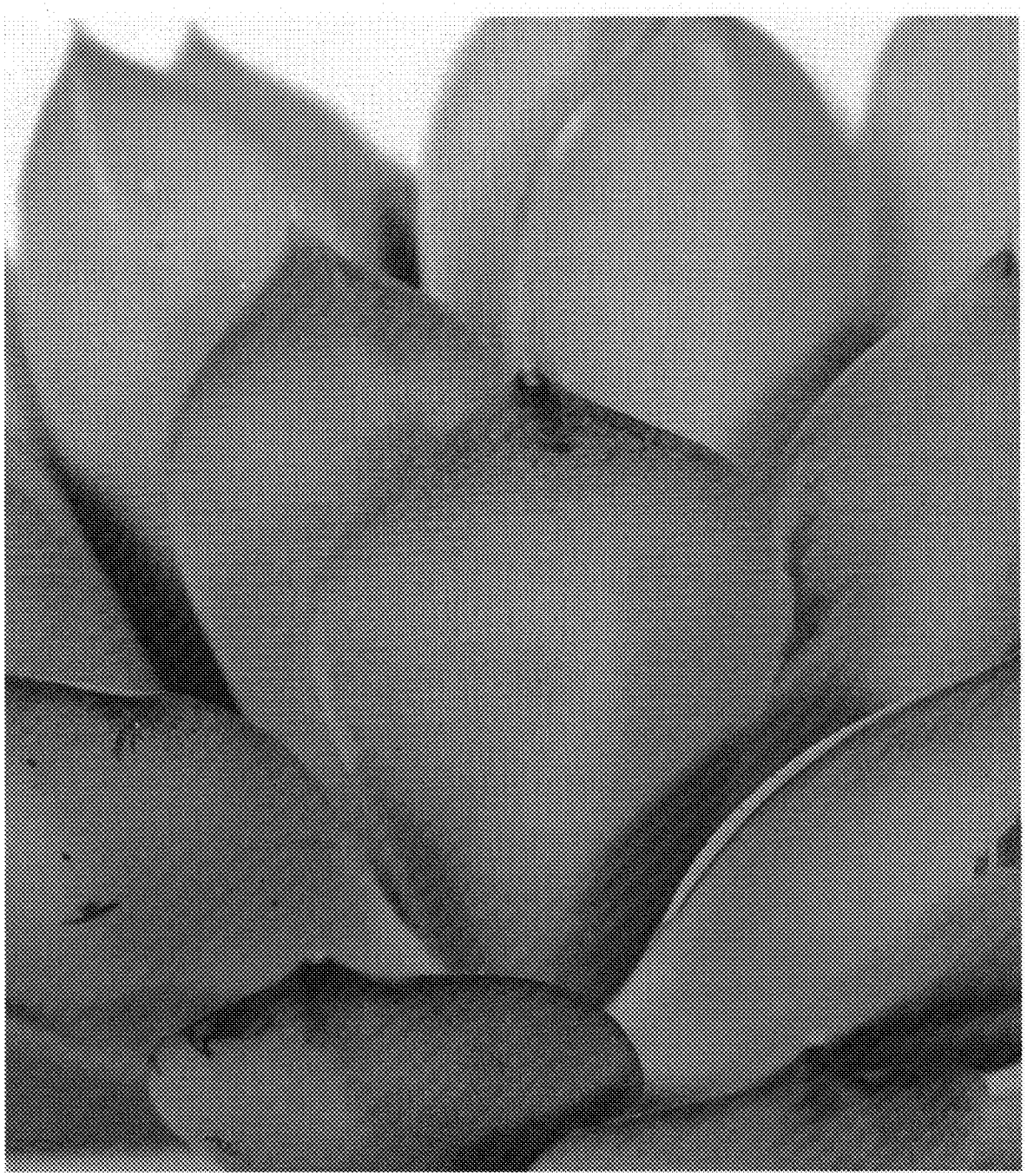
FIG. 4 illustrates, as nearly true as it is reasonably possible to make the same in color photographs of this type, the abaxial surface of the mature foliage 'OVPEARLS14'.

The following observations and measurements made in December of 2021 describe averages from a sample set of six specimens of 1 year old 'OVPEARLS14' plants grown in 8.5 cm nursery containers at commercial greenhouse in Bleiswijk, the Netherlands. Plants were produced using conventional greenhouse production protocols for *Echeveria* which consisted of minimal subsurface irrigation, fertilizer applications, and chemical pest control measures against thrips as required. No other chemical pest and disease control measures were taken. Plants were grown under approximately 50 percent shade after propagation and later exposed to full sun once they began to mature. No photoperiodic treatments or artificial light was given to the plants.

Those skilled in the art will appreciate that certain characteristics will vary with older or, conversely, with younger plants. 'OVPEARLS14' has not been observed under all possible environmental conditions. Where dimensions, sizes, colors and other characteristics are given, it is to be understood that such characteristics are approximations or averages set forth as accurately as practicable. The phenotype of the variety may differ from the descriptions set forth herein with variations in environmental, climatic and cultural conditions. Color notations are based on *The Royal Horticultural Society Colour Chart,* The Royal Horticultural Society, London, 2015 (sixth edition).

A botanical description of 'OVPEARLS14' and a comparison with the parent plants and closest known comparator is provided below.

Plant description:

*Growth habit*.—Succulent perennial with foliage growing in a compact, non-branched basal rosette, eventually forms a short stem with age.

*Plant form*.—Globular.

*Height from soil level to top of foliar plane*.—10.8 cm.

*Plant spread*.—Average of 19.8 cm.

*Growth rate*.—Moderately fast.

*Plant vigor*.—Moderately to highly vigorous.

*Propagation*.—Type — Leaf cuttings. Time to initiate rooting — Approximately 5 weeks at an approximate temperature of 21 degrees Celsius. Crop time — Approximately 1 year to produce a marketable plant in a 7 cm container.

*Disease and pest resistance or susceptibility*.—Neither resistance nor susceptibility to typical *Echeveria* pests and diseases has been observed.

*Environmental tolerances*.—Adapt to, at least, USDA Zones 10 to 12 and temperatures as high as 40 degrees Celsius; moderate tolerance to rain yet drought tolerant once established; high tolerance to wind.

Root system:

*General*.—Fine, well-branched fibrous roots.

Stems:

*Branching habit*.—Leaves in a non-branching basal rosettes; no main branches or lateral branches present.

Foliage:

*Arrangement*.—Rosette.

*Division*.—Simple.

*Attachment*.—Sessile.

*Quantity*.—Approximately 120 leaves per rosette.

*Shape*.—Oblanceolate.

*Dimensions*.—8.2 cm long, 2.7 cm wide, and 0.7 cm thick, on average.

*Aspect*.—Very slightly concave and curved upwards.

*Attitude*.—Juvenile foliage at the center of the rosette exhibits a near-vertical attitude; foliage becomes progressively more relaxed as it matures and becomes nearly horizontal to slightly pendulous at the outer whorls of the rosette.

*Apex*.—Apiculate.

*Base*.—Long cuneate.

*Margin*.—Entire; occasionally very lightly crenulate to denticulate, usually along one side of the lamina, at and near the apex.

*Pubescence, texture and luster of the adaxial surface*.—Glabrous, smooth, and matte; strongly glaucous.

*Pubescence, texture and luster of the abaxial surface*.—Glabrous, smooth, and matte; strongly glaucous.

*Color*.—Juvenile foliage, adaxial surface — Nearest to in between green and greyed-green, nearest to RHS NN137D and 189A; fading to yellow-green towards the base, nearest to RHS 146D; margined greyed-green, nearest to RHS 194D; apical margins and laminar tip are lightly suffused with greyed-purple, nearest to RHS 186B. Leaves are covered with a thin layer of epicuticular wax which is colored greyed-green, nearest to in between RHS 188A and N189C. Juvenile foliage, abaxial surface — Greyed-green, nearest to RHS 191A; fading lighter towards the base, nearest to RHS 193A; margined yellow-green, nearest to a mixture RHS 145C and 145D; laminar tip is lightly suffused with greyed-purple, nearest to RHS 186B. Leaves are covered with a thin layer of epicuticular wax which is colored greyed-green, nearest to RHS N189C. Mature foliage, adaxial surface — Nearest to a mixture of green and greyed-green, RHS NN137C and 191A, and lightly suffused with 197B; fading to yellow-green towards the base, nearest to RHS 147C; margins are yellow-green, nearest to RHS 146C, and become suffused with greyed-orange distally, nearest to a combination of RHS 176A and 176B; laminar tip is greyed-purple, RHS 187A. Leaves are covered with a thin layer of epicuticular wax which is colored greyed-green, nearest to in between RHS 188A and N189C. Mature foliage, abaxial surface — Nearest to a mixture of yellow-green and greyed-green, RHS 148B and 197A; fading to yellow-green towards the base, nearest to RHS 148B; margins are yellow-green, nearest to RHS 147C, and become suffused with greyed-orange distally, nearest to in between RHS 177A and 200B; laminar tip is greyed-purple, RHS 187A. Leaves are covered with a thin layer of epicuticular wax which is colored greyed-green, nearest to RHS N189C.

*Venation*.—Pattern — No venation is visible. Color, adaxial surface — No venation is visible. Color, abaxial surface — No venation is visible.

*Petiole*.—No petiole; leaves are sessile.

Inflorescence: No flowering has been observed to date.

Comparisons With the Parent Plant

Plants of the new cultivar 'OVPEARLS14' differ from the seed parent, an unnamed *Echeveria pulidonis* plant (not patented) in the following characteristics described in Table 1 below.

TABLE 1

| Characteristic | 'OVPEARLS14' | The seed parent. |
|---|---|---|
| Foliage size. | Longer than the parent. | Smaller than 'OVPEARLS14'. |
| Foliage length. | Longer than the parent. | Shorter than 'OVPEARLS14'. |
| General coloration of the mature foliage. | Generally appearing as blue-grey. | Generally appearing as a light shade of greyed-green. |
| General coloration of the foliar margins. | Apical margins are greyed-orange; the laminar tips are greyed-purple. | Apical margins and laminar tip are a dark shade of greyed-red. |

Plants of the new cultivar 'OVPEARLS14' differ from the pollen parent, an unnamed *Echeveria gibbiflora* plant (not patented) in the following characteristics described in Table 2 below.

TABLE 2

| Characteristic | 'OVPEARLS14' | The pollen parent. |
|---|---|---|
| Foliage abundance. | More abundant than the pollen parent. | Less abundant than 'OVPEARLS14'. |
| Foliage shape. | Oblanceolate. | Broadly obovate. |
| Foliage length. | Longer than the pollen parent. | Shorter than 'OVPEARLS14'. |
| General coloration of the foliage. | Generally appearing as blue-grey. | Blue-grey and heavily suffused with red-purple. |

Comparisons With the Closest Known Comparator

Plants of the new cultivar 'OVPEARLS14' differ from *Echeveria* hybrid 'OVPEARLS12' (U.S. patent application Ser. No. 17/803,288 filed concurrently), which is the closest known comparator, in the following characteristics described in Table 3 below.

TABLE 3

| Characteristic | 'OVPEARLS12' | 'OVPEARLS14' |
|---|---|---|
| Plant size. | Larger than 'OVPEARLS12'. | Smaller than 'OVPEARLS14'. |
| Foliage abundance. | Less abundant than 'OVPEARLS12'. | More abundant than 'OVPEARLS14'. |
| Foliage shape. | Oblanceolate. | Oblanceolate to narrowly oblong. |
| Foliage size. | Larger than 'OVPEARLS12'. | Smaller than 'OVPEARLS14'. |
| Foliar margins. | Occasionally very lightly crenulate to denticulate, usually along one side of the lamina, at and near the apex. | Occasionally with some slight undulation along one side of the lamina, at and near the apex. |

That which is claimed is:

1. A new and distinct variety of *Echeveria pulidonis* x *gibbiflora* plant named 'OVPEARLS14', substantially as described and illustrated herein.

* * * * *